United States Patent
Vail

(10) Patent No.: US 7,918,293 B1
(45) Date of Patent: Apr. 5, 2011

(54) METHOD AND SYSTEM FOR PERCEIVING A BOUNDARY BETWEEN A FIRST REGION AND A SECOND REGION OF A SUPERABRASIVE VOLUME

(75) Inventor: Michael A. Vail, Genola, UT (US)

(73) Assignee: US Synthetic Corporation, Orem, UT (US)

( * ) Notice: Subject to any disclaimer, the term of this patent is extended or adjusted under 35 U.S.C. 154(b) by 757 days.

(21) Appl. No.: 11/370,425

(22) Filed: Mar. 8, 2006

Related U.S. Application Data

(60) Provisional application No. 60/660,138, filed on Mar. 9, 2005.

(51) Int. Cl.
*E21B 10/26* (2006.01)
*C23C 16/26* (2006.01)

(52) U.S. Cl. .............. 175/434; 175/420.2; 175/430; 427/249.8

(58) Field of Classification Search .......... 250/302, 250/303, 306–308, 310; 427/249.8, 249.15, 427/249.17, 255.1, 546, 574, 576, 577, 579, 427/588–590; 51/295, 297, 307–309; 156/89.15, 156/89.27; 423/345; 175/374, 434, 420.2, 175/424, 430
See application file for complete search history.

(56) References Cited

U.S. PATENT DOCUMENTS

| | | | |
|---|---|---|---|
| 2,895,888 A * | 7/1959 | Varner | 205/84 |
| 3,271,572 A * | 9/1966 | Lieber et al. | 250/388 |
| 3,364,354 A * | 1/1968 | Fries | 250/308 |
| 3,519,824 A * | 7/1970 | Weinstock et al. | 250/358.1 |
| 3,639,763 A * | 2/1972 | Streng | 250/308 |
| 3,720,833 A * | 3/1973 | Hay | 250/308 |
| 3,745,623 A | 7/1973 | Wentorf, Jr. et al. | |
| 3,754,138 A * | 8/1973 | Kurstedt et al. | 250/302 |
| 3,769,511 A * | 10/1973 | Delacy | 250/303 |
| 4,079,237 A * | 3/1978 | Schlesinger | 702/172 |
| 4,089,054 A * | 5/1978 | Ott | 250/308 |
| 4,155,009 A * | 5/1979 | Lieber et al. | 250/308 |
| 4,224,380 A | 9/1980 | Bovenkerk et al. | |
| 4,293,767 A * | 10/1981 | Fischer et al. | 250/308 |
| 4,406,948 A * | 9/1983 | Fischer et al. | 250/308 |
| 4,437,012 A * | 3/1984 | Cavy et al. | 250/491.1 |
| 4,441,022 A * | 4/1984 | Joffe et al. | 850/55 |
| 4,467,198 A * | 8/1984 | Joffe et al. | 250/308 |
| 4,832,708 A | 5/1989 | Csillag | |

(Continued)

FOREIGN PATENT DOCUMENTS

JP 59-219500 12/1984

*Primary Examiner* — Bernard E Souw
(74) *Attorney, Agent, or Firm* — Holland & Hart, LLP

(57) ABSTRACT

Methods of evaluating a superabrasive volume or a superabrasive compact are disclosed. One method may comprise exposing a superabrasive volume to beta particles and detecting a quantity of scattered beta particles. Further, a boundary may be perceived between a first region and a second region of the superabrasive volume in response to detecting the quantity of scattered beta particles. In another embodiment, a boundary between a catalyst-containing region and a catalyst-diminished region of a polycrystalline diamond volume may be perceived. In a further embodiment, a boundary may be perceived between a catalyst-containing region and a catalyst-diminished region of a polycrystalline diamond compact. Additionally, a depth to which a catalyst-diminished region extends within a polycrystalline diamond volume of a polycrystalline diamond compact may be measured in response to detecting a quantity of scattered beta particles. A system configured to evaluate a superabrasive volume is disclosed.

25 Claims, 16 Drawing Sheets

U.S. PATENT DOCUMENTS

| | | | |
|---|---|---|---|
| 5,119,540 A * | 6/1992 | Kong et al. | 118/730 |
| 5,469,927 A | 11/1995 | Griffin | |
| 5,583,343 A * | 12/1996 | Dilmanian et al. | 250/475.2 |
| 5,607,489 A * | 3/1997 | Li | 51/309 |
| 6,029,502 A * | 2/2000 | Stuker | 73/37.7 |
| 6,344,149 B1 * | 2/2002 | Oles | 216/11 |
| 6,363,787 B1 * | 4/2002 | Carlson et al. | 73/579 |
| 6,544,308 B2 | 4/2003 | Griffin et al. | |
| 6,585,064 B2 | 7/2003 | Griffin et al. | |
| 6,589,640 B2 | 7/2003 | Griffin et al. | |
| 6,592,985 B2 | 7/2003 | Griffin et al. | |
| 6,739,214 B2 | 5/2004 | Griffin et al. | |
| 6,749,033 B2 | 6/2004 | Griffin et al. | |
| 6,797,326 B2 | 9/2004 | Griffin et al. | |
| 7,128,974 B2 * | 10/2006 | Scarsbrook et al. | 428/408 |
| 7,864,919 B1 | 1/2011 | Eyre et al. | |
| 2005/0241239 A1 * | 11/2005 | Sung | 51/308 |
| 2006/0122306 A1 * | 6/2006 | Stafford et al. | 524/440 |
| 2006/0157285 A1 * | 7/2006 | Cannon et al. | 175/374 |
| 2006/0288756 A1 * | 12/2006 | De Meurechy | 73/1.01 |
| 2007/0023206 A1 * | 2/2007 | Keshavan et al. | 175/374 |
| 2008/0023231 A1 * | 1/2008 | Vail | 175/434 |
| 2008/0206576 A1 * | 8/2008 | Qian et al. | 428/446 |
| 2010/0326741 A1 * | 12/2010 | Patel | 175/431 |

* cited by examiner

METHOD AND SYSTEM FOR PERCEIVING A BOUNDARY BETWEEN A FIRST REGION AND A SECOND REGION OF A SUPERABRASIVE VOLUME

CROSS-REFERENCE TO RELATED APPLICATION

This application claims the benefit of U.S. Patent Application No. 60/660,138, filed 9 Mar. 2005, the disclosure of which is incorporated, in its entirety, by this reference.

BACKGROUND

Superabrasive compacts are utilized for a variety of applications and in a corresponding variety of mechanical systems. Such superabrasive compacts may be known in the art as inserts, buttons, machining tools, wear elements, or bearing elements and may be typically manufactured by forming a superabrasive layer on the end of a substrate (e.g., a sintered or cemented tungsten carbide substrate). As an example, polycrystalline diamond, or other suitable superabrasive material, such as cubic boron nitride, may be sintered onto the surface of a cemented carbide substrate under an ultra-high pressure and ultra-high temperature ("HPHT") process to form a superabrasive compact, as described in greater detail below. Polycrystalline diamond elements are used in drilling tools (e.g., inserts, cutting elements, gage trimmers, etc.), machining equipment, bearing apparatuses, wire drawing machinery, and in other mechanical systems. For instance, polycrystalline diamond compacts (PDCs) have found utility as cutting elements in drill bits (e.g., roller cone drill bits and fixed cutter drill bits).

Explaining further, such PDCs typically include a diamond layer or table formed by a sintering process employing HPHT conditions that causes the diamond table to become bonded or affixed to a substrate (such as cemented tungsten carbide substrate), as described in greater detail below. Optionally, the substrate may be brazed or otherwise joined to an attachment member such as a stud or to a cylindrical backing, if desired. Generally, a rotary drill bit may include a plurality of polycrystalline abrasive cutting elements affixed to the drill bit body. Each PDC may be employed as a subterranean cutting element mounted to a drill bit either by press-fitting, brazing, or otherwise coupling a stud to a recess defined by the drill bit, or by brazing the cutting element directly into a preformed pocket, socket, or other receptacle formed in the subterranean drill bit. In one example, cutter pockets may be formed in the face of a matrix-type bit comprising tungsten carbide particles that are infiltrated or cast with a binder (e.g., a copper-based binder), as known in the art. Such subterranean drill bits are typically used for rock drilling and for other operations which require high abrasion resistance or wear resistance.

A PDC is normally fabricated by placing a cemented carbide substrate into a container or cartridge with a layer of diamond crystals or grains positioned adjacent one surface of a substrate. A number of such cartridges may be typically loaded into an ultra-high pressure press. The substrates and adjacent diamond crystal layers are then sintered under HPHT conditions. The HPHT conditions cause the diamond crystals or grains to bond to one another to form polycrystalline diamond. In addition, as known in the art, a catalyst may be employed for facilitating formation of polycrystalline diamond. In one example, a so-called "solvent catalyst" may be employed for facilitating the formation of polycrystalline diamond. For example, cobalt, nickel, and iron are among examples of solvent catalysts for forming polycrystalline diamond. In one configuration, during sintering, solvent catalyst comprising the substrate body (e.g., cobalt from a cobalt-cemented tungsten carbide substrate) becomes liquid and sweeps from the region adjacent to the diamond powder and into the diamond grains. Of course, a solvent catalyst may be mixed with the diamond powder prior to sintering, if desired. Also, as known in the art, such a solvent catalyst may dissolve carbon. Such carbon may be dissolved from the diamond grains or portions of the diamond grains that graphitize due to the high temperatures of sintering. When the solvent catalyst is cooled, the carbon held in solution may precipitate or otherwise be expelled from the solvent catalyst and may facilitate formation of diamond bonds between abutting or adjacent diamond grains. Thus, diamond grains become mutually bonded to form a polycrystalline diamond table upon the substrate. A conventional process for forming polycrystalline diamond cutters is disclosed in U.S. Pat. No. 3,745,623 to Wentorf, Jr. et al., the disclosure of which is incorporated herein, in its entirety, by this reference. Optionally, another material may replace the solvent catalyst that has been at least partially removed from the polycrystalline diamond.

Solvent catalyst in the polycrystalline diamond may be detrimental. For instance, because the solvent catalyst exhibits a much higher thermal expansion coefficient than the diamond structure, the presence of such solvent catalyst within the diamond structure is believed to be a factor leading to premature thermal mechanical damage. Accordingly, as the polycrystalline diamond reaches temperatures exceeding 400° Celsius, the differences in thermal expansion coefficients between the diamond and the solvent catalyst may cause diamond bonds to fail. Of course, as the temperature increases, such thermal mechanical damage may be increased. In addition, as the temperature of the polycrystalline diamond layer approaches 750° Celsius, a different damage mechanism may initiate. At approximately 750° Celsius or greater, the solvent catalyst may interact with the diamond to cause graphitization of the diamond. Such graphitization is believed to contribute to or cause mechanical damage within the polycrystalline diamond. This phenomenon may be termed "back conversion," meaning conversion of diamond to graphite. Such conversion from diamond to graphite may cause dramatic loss of wear resistance in a polycrystalline diamond compact and may rapidly lead to insert failure. Accordingly, as known in the art, the solvent catalyst in the polycrystalline diamond layer may be at least partially removed from the polycrystalline diamond. For instance, the solvent catalyst may be at least partially removed from the polycrystalline diamond by acid leaching.

Accordingly, a superabrasive volume may include at least two regions with differing constituents. Thus, it may be advantageous to determine or perceive different regions of a superabrasive volume. For instance, such perception may allow for monitoring of (i.e., quality control) relative to superabrasive apparatus manufacturing and processing methods. Thus, it would be advantageous to provide methods and systems for evaluating (e.g., nondestructively) different regions of a superabrasive volume.

SUMMARY

The present invention relates generally to observing interaction between beta particles and a superabrasive volume, a superabrasive compact, or a superabrasive article. More particularly, at least one characteristic of a superabrasive volume or layer may be determined by detecting scattered beta particles. Further, a boundary may be perceived in response to detecting a quantity of scattered beta particles. In one embodiment, a superabrasive may comprise a polycrystalline diamond. Optionally, a catalyst used for forming the polycrystalline diamond volume may be at least partially removed from a region of the polycrystalline diamond volume. In one example, a depth to which a catalyst has been at least partially removed from a region of a superabrasive volume (e.g., a polycrystalline diamond volume) may be measured.

One aspect of the present invention relates to a method of evaluating a superabrasive volume. Particularly, the method may comprise exposing a superabrasive volume to beta particles and detecting a quantity of scattered beta particles. Further, a boundary (e.g., at least a portion of a boundary surface) may be perceived between a first region of the superabrasive volume and a second region of the superabrasive volume in response to detecting the quantity of scattered beta particles.

Another aspect of the present invention relates to a method of evaluating a polycrystalline diamond volume. Specifically, such a method may comprise exposing a polycrystalline diamond volume to beta particles and detecting a quantity of scattered beta particles. In addition, a boundary may be perceived between a catalyst-containing region of the polycrystalline diamond volume and a catalyst-diminished region of the polycrystalline diamond volume in response to detecting the quantity of scattered beta particles.

A further aspect of the present invention relates to a method of evaluating a polycrystalline diamond compact. For example, a polycrystalline diamond compact comprising a polycrystalline diamond volume bonded to a substrate may be provided. In addition, the polycrystalline diamond volume may be exposed to beta particles and a quantity of scattered beta particles may be detected. Also, a boundary may be perceived between a catalyst-containing region of the polycrystalline diamond volume and a catalyst-diminished region of the polycrystalline diamond volume in response to detecting the quantity of scattered beta particles.

Another aspect of the present invention relates to a method of evaluating a polycrystalline diamond compact. Particularly, a polycrystalline diamond compact may be provided, the polycrystalline diamond compact comprising a polycrystalline diamond volume bonded to a substrate. Also, the polycrystalline diamond volume may be exposed to beta particles and a quantity of scattered beta particles may be detected. A depth to which a catalyst-diminished region of the polycrystalline diamond extends within the polycrystalline diamond volume may be measured in response to detecting the quantity of scattered beta particles.

Yet an additional aspect of the present invention relates to a system configured to evaluate a superabrasive volume. For instance, the system may comprise a beta particle source, a beta particle detector, and calibration data or standards for correlating a quantity of detected beta particles (e.g., scattered beta particles) to an indicated depth of a first region of a superabrasive volume.

Features from any of the above mentioned embodiments may be used in combination with one another, without limitation. In addition, other features and advantages of the instant disclosure will become apparent to those of ordinary skill in the art through consideration of the ensuing description, the accompanying drawings, and the appended claims.

BRIEF DESCRIPTION OF THE DRAWINGS

Further features of the subject matter of the instant disclosure, its nature, and various advantages will be more apparent from the following detailed description and the accompanying drawings, which illustrate various exemplary embodiments, are representations, and are not necessarily drawn to scale, wherein.

DETAILED DESCRIPTION

Generally, a superabrasive volume may include at least two different regions. For example, a superabrasive volume may be formed by a HPHT sintering process to include different regions of differing composition. In another embodiment, a superabrasive volume may be formed by a HPHT process and may be subsequently treated to remove at least one constituent (e.g., a catalyst) from a selected region of the superabrasive volume. In yet a further embodiment, a superabrasive layer or volume may be formed by a chemical process (e.g., chemical vapor deposition) or other processes under varying conditions and employing different constituents to form at least two regions within the superabrasive layer or volume.

The present invention relates generally to observing interaction between beta particles and a superabrasive volume to perceive a boundary between two regions within the superabrasive volume or between a superabrasive volume and a substrate. The phrase "beta particles," as used herein, refers to electrons emitted by unstable atomic nuclei in response to neutron decay (e.g., where a neutron decays into a proton and an electron). As known in the art, beta particles (which may also be referred to as beta radiation) may comprise positrons (i.e., so-called "antielectrons" which are identical to electrons but carry a positive electrical charge). Accordingly, beta particles are electrons which may be emitted from radioisotopes. The present invention contemplates that if beta particles interact with a superabrasive volume, at least some of the beta particles may be scattered (e.g., reflected or "backscattered") generally toward the beta particle source. Such backscattered beta particles may be measured with a detector (e.g., a Geiger-Mueller tube) and such a measurement may be employed for perception of a boundary between a first region of the superabrasive volume and a second region of a superabrasive volume. The term "superabrasive," as used herein, refers to any material having a hardness that is at least equal to a hardness of tungsten carbide. For example, polycrystalline diamond and cubic boron nitride are each a superabrasive material.

Accordingly, the present invention contemplates that a system configured to emit and detect beta particles may be employed for perceiving a boundary between a first region of a superabrasive volume and a second region of a superabrasive volume of the superabrasive volume. More particularly, a system configured to emit and detect beta particles may comprise a beta particle source (e.g., a radioisotope). For example, in one embodiment, a beta particle source may comprise thallium. Beta particle emission and detection systems are commercially available from UPA Technology of West Chester Ohio.

Figure 1:
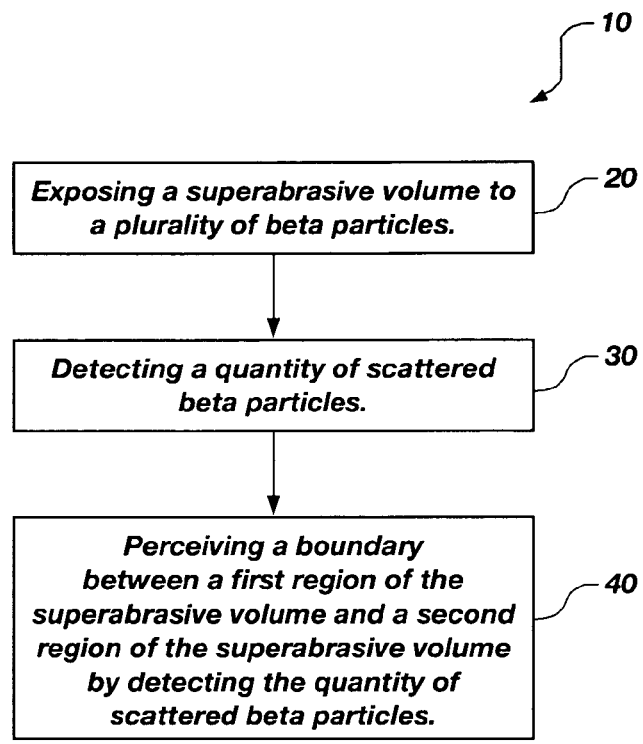
FIG. 1 shows a schematic flow chart of one embodiment of a method of evaluating a superabrasive volume comprising a first region and a second region.

For instance, FIG. 1 shows a schematic flow chart of one embodiment of a method 10 of evaluating a superabrasive volume. More particularly, a beta particle exposure process 20 may comprise exposing a superabrasive volume to a plurality of beta particles. Further, a beta particle detection process 30 may comprise detecting a quantity of scattered (e.g., backscattered) beta particles. For example, a beta detection process 30 may detect a quantity of scattered beta particles for a selected amount of time during which a superabrasive volume is exposed to beta particles. In addition, in boundary perception process 40, a boundary may be perceived between a first region of the superabrasive volume and a second region of the superabrasive volume by detecting the quantity of scattered beta particles.

Explaining further, a first region of a superabrasive volume and a second region of the superabrasive volume may differ in composition. Thus, the boundary may define or delineate the first region and the second region. In further detail, a first region and a second region of a superabrasive volume may include constituents that differ in atomic number. For example, a first region of a superabrasive volume may include at least one constituent exhibiting an atomic number that differs by at least about 20% from an atomic number of at least one constituent of a second region of a superabrasive volume. More particularly, in one embodiment, a plurality of beta particles may, in general, travel through a first region of a superabrasive volume exhibiting a relatively lower average atomic number (i.e., a relatively lower density) without significant scattering and may be significantly scattered by a second region of a superabrasive volume exhibiting a relatively higher average atomic number (i.e., a relatively higher density). In one example, a depth of at least one of a first region and a second region of a superabrasive volume may be measured.

In one embodiment, the superabrasive volume may comprise a plurality of super-hard particles or superabrasive grains that are mutually bonded to one another to form a coherent skeleton or matrix structure. For example, a superabrasive volume may comprise polycrystalline diamond, cubic boron nitride, or any other superabrasive as known in the art, without limitation. One of ordinary skill in the art will appreciate that a first region and a second region of a superabrasive volume may be formed by different processes, with different materials, by changing a composition of at least one of the first and second regions, or by combinations or variations of the foregoing.

Figure 2:
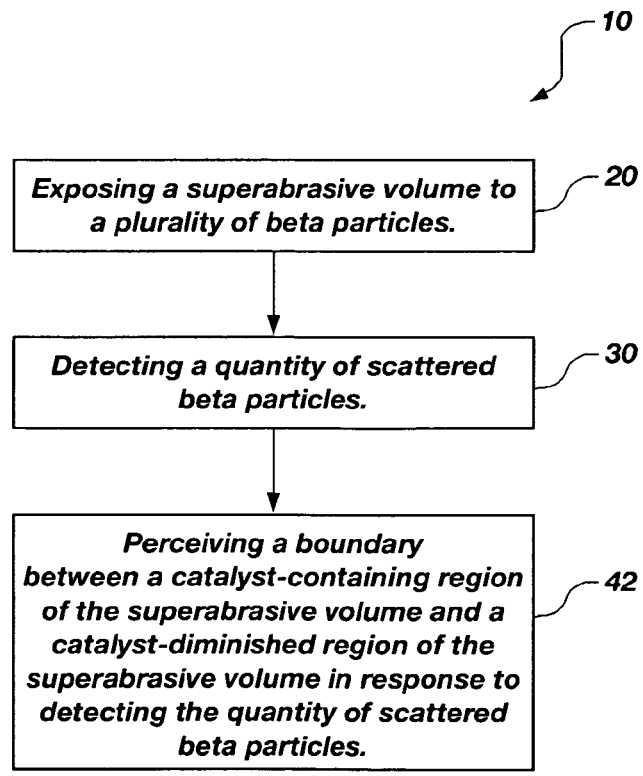
FIG. 2 shows a schematic flow chart of one embodiment of a method of evaluating a superabrasive volume comprising a catalyst-containing region and a catalyst-diminished region.

For example, as explained above, a superabrasive volume may be formed by employing a so-called catalyst, which may facilitate grain-to-grain bonding. Further, subsequent to formation of the superabrasive volume in the presence of a catalyst, at least a portion of the catalyst may be removed from a selected region of the coherent skeleton or matrix structure of the superabrasive volume. Thus, a superabrasive volume may comprise a catalyst-containing region and a catalyst-diminished region, wherein a boundary is defined between the regions. As shown in FIG. 2, the present invention contemplates a method 10 for evaluating a superabrasive volume to perceive a boundary between a catalyst-containing region of a superabrasive volume and a catalyst-diminished region of the superabrasive volume. Particularly, such a superabrasive volume may be exposed to a plurality of beta particles (i.e., in beta particle exposure process 20) and a quantity of scattered beta particles may be detected (i.e., in beta particle detection process 30). Furthermore, a boundary may be perceived (i.e., in a boundary perception process 42) between a catalyst-containing region of the superabrasive volume and a catalyst-diminished region of the superabrasive volume in response to detecting the quantity of scattered beta particles.

Figure 3:
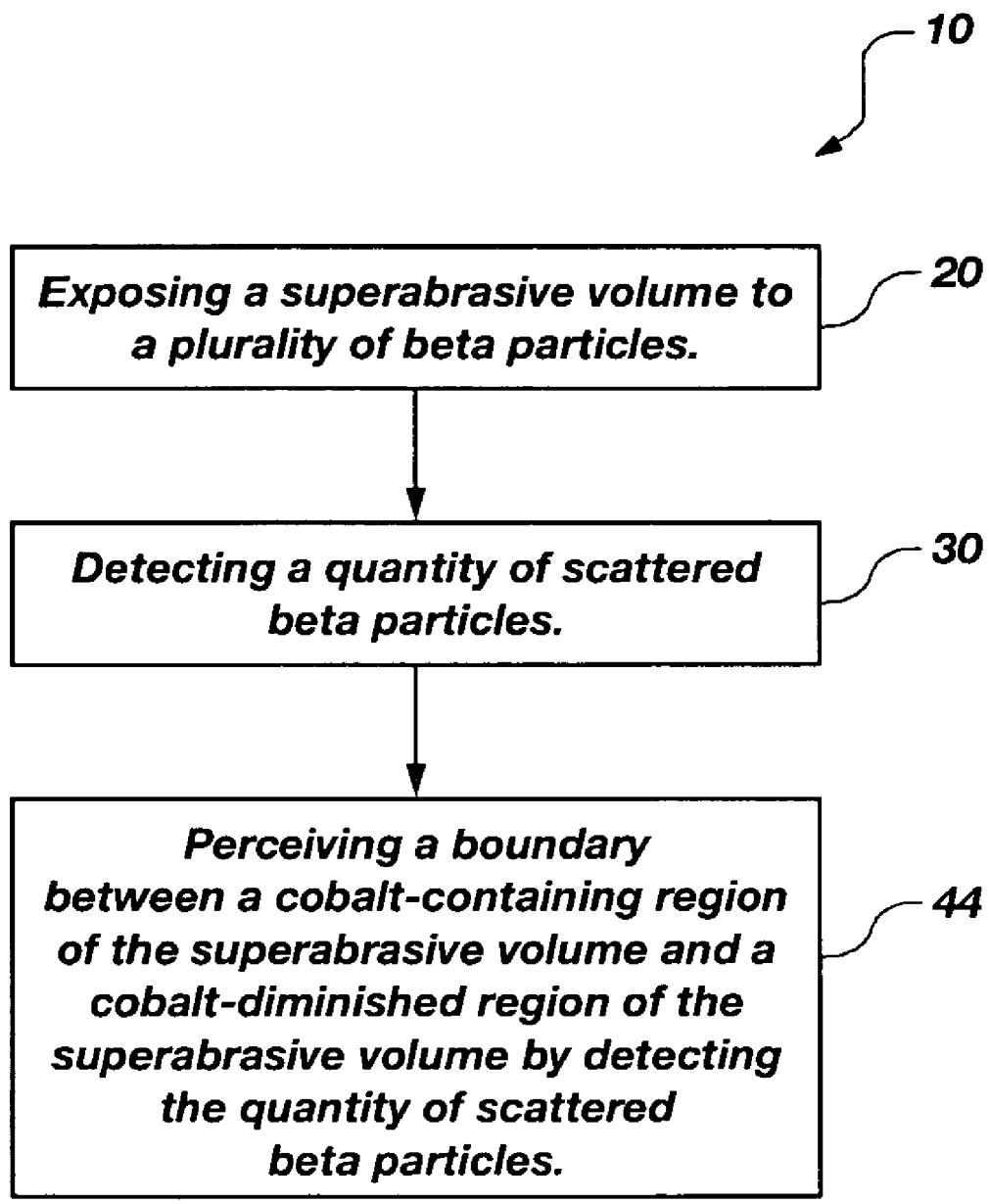
FIG. 3 shows a schematic flow chart of one embodiment of a method of evaluating a superabrasive volume comprising a cobalt-containing region and a cobalt-diminished region.

In another embodiment, a superabrasive volume may be formed with a catalyst comprising cobalt. Further, a region of the superabrasive volume may be formed, wherein the region is at least partially diminished or depleted of cobalt. Removal of at least a portion of cobalt from a selected region of the superabrasive volume may be accomplished by acid leaching, a plating process, another chemical process, or any other process as known in the art. Optionally, a region of a superabrasive volume may be formed without cobalt (i.e., a catalyst). For example, a first region of a superabrasive volume may be formed via HPHT sintering, while a second region of the superabrasive volume may be formed by chemical vapor deposition ("CVD"). As shown in FIG. 3, relative to a superabrasive volume that includes at least one region comprising cobalt, a method 10 of evaluating a superabrasive volume to perceive a boundary between a cobalt-containing region of a superabrasive volume and a cobalt-diminished region of a superabrasive volume. Particularly, a superabrasive volume may be exposed to a plurality of beta particles in a beta particle exposure process 20 and a quantity of scattered beta particles may be detected in a beta particle detection process 30. In addition, in a boundary perception process 44, a boundary between a cobalt-containing region of the superabrasive volume and a cobalt-diminished region of the superabrasive volume may be perceived by detecting the quantity of scattered beta particles.

Figure 4:
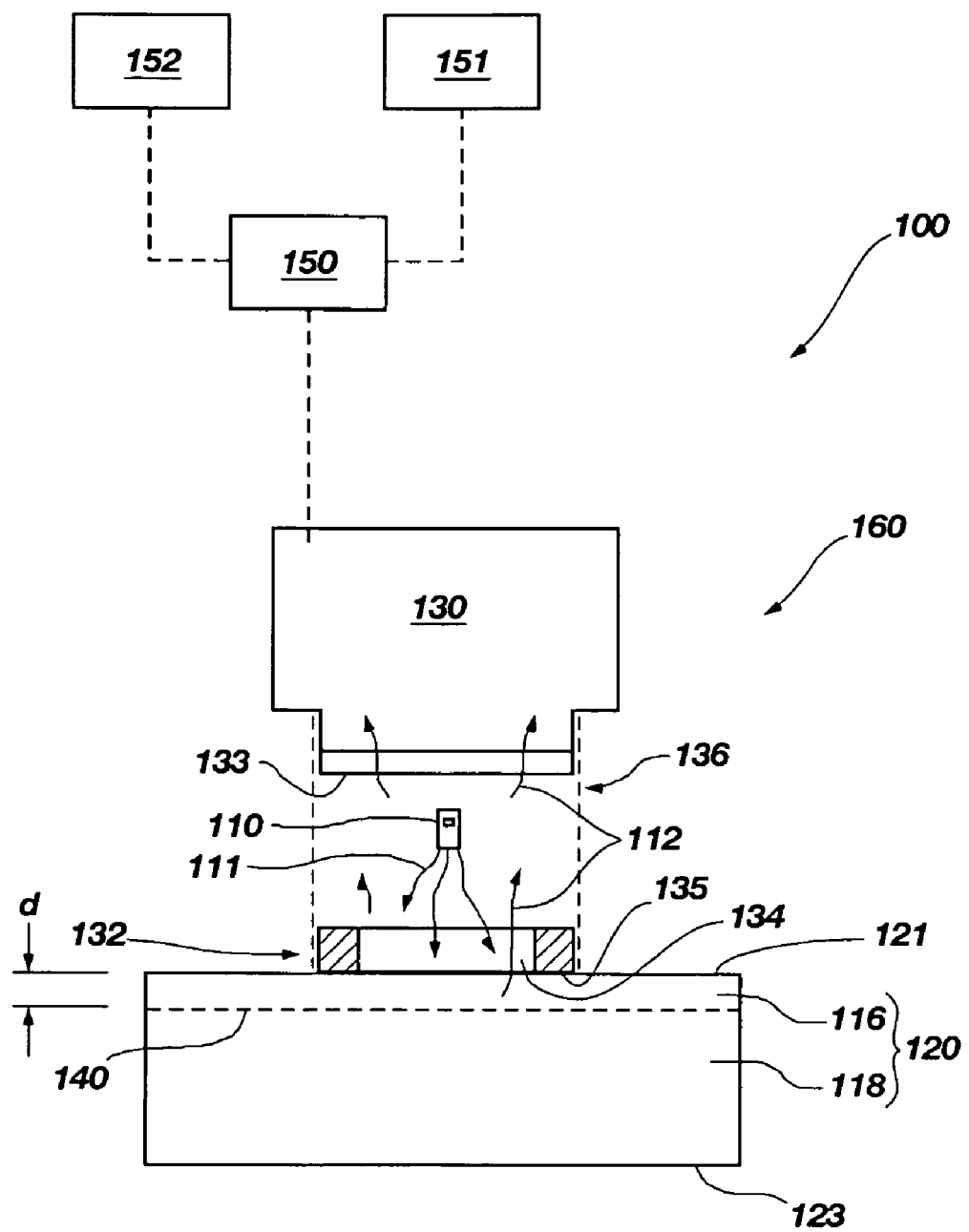
FIG. 4 shows a schematic, cross-sectional view of a beta particle evaluation system during use in evaluating a superabrasive volume.

Further, the present invention contemplates that a beta particle generation and detection system may be utilized for exposing a superabrasive volume to beta particles, detecting scattered beta particles, and perceiving a boundary between a first region of a superabrasive volume and a second region of a superabrasive volume. For example, FIG. 4 shows a schematic, cross-sectional representation of a beta particle evaluation system 100 comprising a beta particle source 110, a beta particle detector 130, and an analysis system 150. In one embodiment, beta particle source 110 may comprise thallium (e.g., radioisotope thallium 204), although any material that emits beta particles, as known in the art, may comprise beta particle source 110, without limitation. One of ordinary skill in the art will appreciate that beta particle source 110 may be selected or tailored so that emitted beta particles exhibit a desired energy level. Accordingly, the present invention contemplates that a suitable beta particle source, relative to a nominal energy level of its emitted beta particles, may be selected so that at least some beta particles interact with an anticipated boundary. In further detail, as shown in FIG. 4, system 100 may include a metering port 132 positioned at a selected distance relative to beta particle source 110. System 100 may be configured so that beta particles generated by beta particle source 110 are directed toward aperture 134 of metering port 132. Optionally, emitted beta particles 111 emitted from beta particle source 110 may be collimated, so that emitted beta particles 111 generally travel within a selected "spot size." Thus, optionally, emitted beta particles 111 may pass through metering port 132 without substantial interaction therewith. In addition, metering port 132 in combination with coupling structure 136 may be configured to inhibit, block, or otherwise interfere with transmission of scattered (e.g., reflected, backscattered, or otherwise influenced to change direction or velocity) beta particles 112 except for those passing through aperture 134 of metering port 132 in a suitable direction to pass into detector 130 through detector surface 133. In one embodiment, beta particle detector 130 may comprise a Geiger-Mueller tube or any other device as known in the art for detecting beta particles.

In one embodiment, analysis system 150 may comprise a computer or any device including at least one processor. Further, at least one input device 151 (e.g., a mouse, a keyboard, etc.) and at least one output device (e.g., a monitor, a printer, a liquid crystal display, etc.) may be operably coupled to analysis system 150. In addition, analysis system 150 may communicate with beta particle detector 130 and may be configured to measure a voltage or other signal from beta particle detector 130 to perceive a boundary within a superabrasive volume (e.g., measure a depth of the boundary from an exterior surface of the superabrasive volume). In one embodiment, analysis system 150 may be configured to determine a quantity of scattered beta particles 112 detected by beta particle detector 130 for a given amount of time. Further, analysis system 150 may be configured to correlate the measured quantity of scattered beta particles to a depth d between lower surface 135 of metering port 132 and a boundary 140 of superabrasive volume 120. As shown in FIG. 4, boundary 140 may comprise a boundary surface between region 116 and region 118. Thus, during operation, lower surface 135 of metering port 132 may be positioned at a known distance from upper surface 121 of superabrasive volume 120. For example, metering port 132 may be positioned adjacent to or abutting upper surface 121 of superabrasive volume 120. Further, emitted beta particles 111 may pass through aperture 134 of metering port 132 and may interact with first region 116 of superabrasive volume 120, second region 118 of superabrasive volume 120, or both to perceive boundary 140 (e.g., at least a portion of a boundary surface) between first region 116 and second region 118. In one embodiment, first region 116 of superabrasive volume 120 may exhibit a density (i.e., an average atomic number) which is less than a density (i.e., an average atomic number) of second region 118 of superabrasive volume 120. Such a configuration may cause emitted beta particles 111 to interact with the portion of second region 118 substantially defining boundary 140. Accordingly, in such a configuration, scattered beta particles 112 may travel toward beta particle detector 130 through aperture 134 of metering port 132. One of ordinary skill in the art will appreciate that as depth d increases, fewer scattered beta particles 112 may be received and detected by beta particle detector 130.

For example, analysis system 150 may be calibrated by exposing a superabrasive volume to a plurality of beta particles, detecting a quantity of scattered beta particles, and determining at least one characteristic of a boundary by a different or independent method. In one embodiment, a superabrasive volume may be destructively evaluated to determine a position or another characteristic (e.g., a size, shape, composition, etc.) of a boundary within a superabrasive volume. Specifically, for example, a superabrasive volume may be analyzed via system 100 and then may be sectioned (i.e., cut or otherwise separated into pieces) and analyzed to determine a depth d at which the boundary is positioned. Such a determination may utilize, without limitation, scanning electron microscopy, x-ray diffraction, or any other analytic processes as known in the art. The present invention further contemplates that a plurality of superabrasive volumes each exhibiting a different depth d at which a boundary is positioned may be analyzed via system 100 and also analyzed via a different method to develop calibration data which analysis system 150 may employ to determine or predict a depth d for a given superabrasive volume.

Explaining further, beta particle evaluation system 100 (e.g., analysis system 150) may comprise a beta particle source 110, a beta particle detector 130, and calibration data for correlating a quantity of detected beta particles to an indicated depth of a first region of a superabrasive volume. In one embodiment, the calibration data may comprise a first measured quantity of scattered beta particles associated with a first depth (e.g., a first depth determined by destructive evaluation of at least one sample) and at least a second measured quantity of scattered beta particles associated with a second depth (e.g., a second depth determined by destructive evaluation of at least one sample). For example, a first depth may be relatively shallow, while a second depth may be of a magnitude near an anticipated upper limit. For example, a first depth may be substantially zero (i.e., an exterior surface of a superabrasive volume may be a boundary), or, may be between about zero and 0.002 inches. As a further example, a second depth may be about 0.005 inches. One of ordinary skill in the art will appreciate that a first and/or second depth may be selected in accordance with a given beta particle source, or vice versa.

In addition, one of ordinary skill in the art will appreciate that once a first measured or detected quantity of scattered beta particles may be correlated to the first depth and a second measured or detected quantity of scattered beta particles may be correlated to a second depth. Further, one of ordinary skill in the art will appreciate that linear regression may be employed (via the first measured depth, first measured quantity of beta particles, the second measured depth, and the second measured quantity of beta particles) to calculate (predict, calculate, or extrapolate) a depth associated with a measured quantity of scattered beta particles that differs from the first or second measured quantity of scattered beta particles. Any regression or predictive algorithm as known in the art may be employed for predicting or calculating a depth of a region of a superabrasive volume based on a detected or measured quantity of scattered beta particles.

Thus, in one embodiment, calibration data may be designed to correlate the quantity of detected, scattered beta particles to the indicated depth of a first region of a polycrystalline diamond volume. In one specific example, the calibration data may be designed to correlate the quantity of detected, scattered beta particles to the indicated depth of a catalyst-diminished region of a polycrystalline diamond volume. In another example, the calibration data may be designed to correlate the quantity of detected, scattered beta particles to the indicated depth of a cobalt-diminished region of a polycrystalline diamond volume. One of ordinary skill in the art will appreciate that a beta particle source is a radioisotope will change in its behavior over time (i.e., less beta particles will be emitted as the radioisotope ages). Therefore, one of ordinary skill in the art will appreciate that calibration should be performed frequently enough to avoid significant errors.

One of ordinary skill in the art will appreciate that many factors may influence behavior of system 100 during use. For example, the material comprising beta particle source 110, the size of metering port 132, the size and configuration of beta particle detector 130, the shape and/or size of the boundary, and/or the composition of the superabrasive volume may influence operational parameters and characteristics of system 100 during use. In addition, differences in composition between first region 116 and second region 118 of a superabrasive volume 120 may influence operational parameters and characteristics of system 100 during use.

Figure 5:
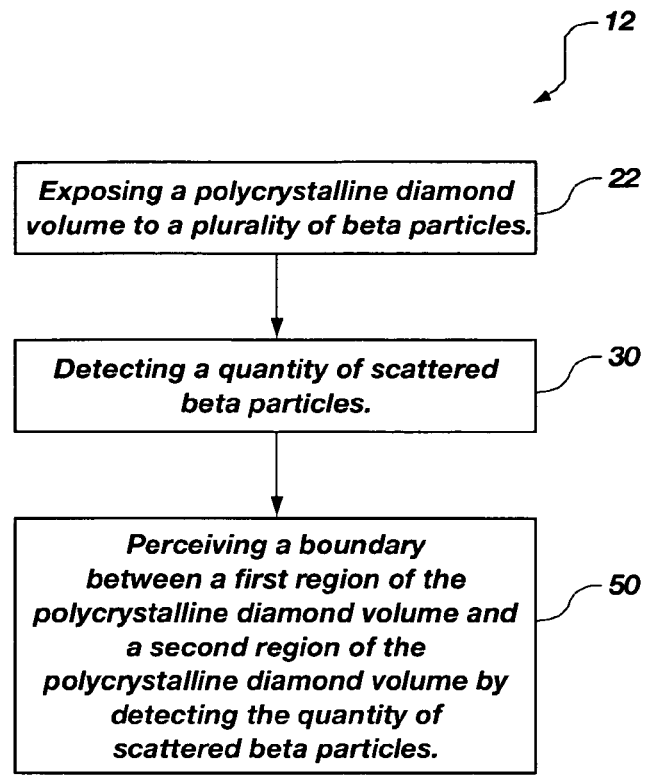
FIG. 5 shows a schematic flow chart of one embodiment of a method of evaluating a polycrystalline diamond volume comprising a first region and a second region.

In one aspect of the present invention, a superabrasive volume (e.g., superabrasive volume 120, as shown in FIG. 4) may comprise polycrystalline diamond. Such polycrystalline diamond may be formed, as described above, by way of a HPHT sintering process. Furthermore, a catalyst may be utilized to form the superabrasive volume, as known in the art. The present invention contemplates that, as shown in FIG. 5, a method 12 for evaluating a polycrystalline diamond volume comprising a beta particle exposure process 22, wherein a polycrystalline diamond volume may be exposed to a plurality of beta particles. In addition, a beta particle detection process 30 may comprise detecting a quantity of scattered beta particles. Further, a boundary may be perceived, in a boundary perception process 50, between a first region of the polycrystalline diamond volume and a second region of the polycrystalline diamond volume by detecting the quantity of scattered beta particles.

Figure 6:
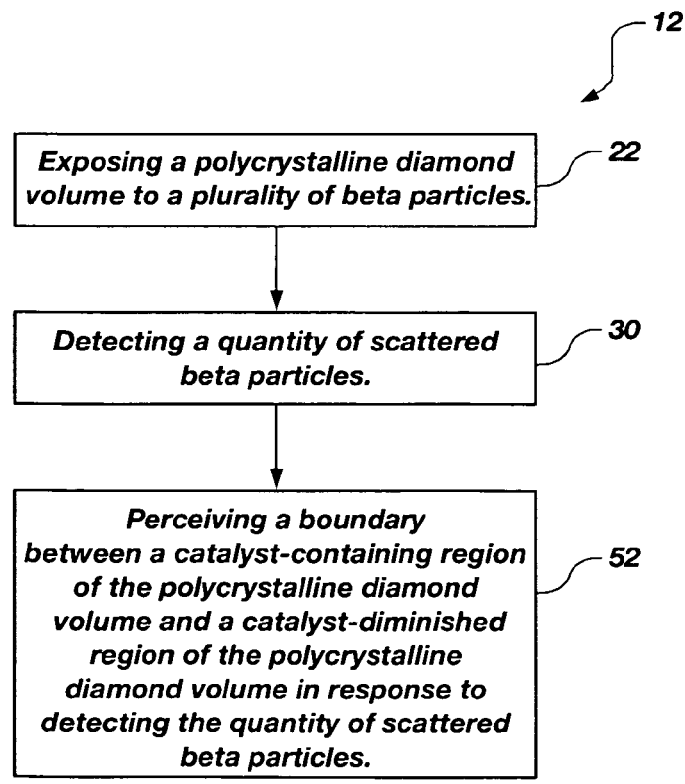
FIG. 6 shows a schematic flow chart of one embodiment of a method of evaluating a polycrystalline diamond volume comprising a catalyst-containing region and a catalyst-diminished region.

In another embodiment, as shown in FIG. 6, the present invention further contemplates a method 12 for evaluating a polycrystalline diamond volume including a catalyst-containing region and a catalyst-diminished region. Generally, method 12 may comprise a beta particle exposure process 22, a beta particle detection process 30, and a boundary perception process 52. For example, catalyst may be at least partially removed from a selected region of a polycrystalline diamond volume by acid leaching, plating processes (e.g., electrolytic or electroless processes), or as otherwise known in the art. More particularly, referring to FIG. 4, region 116 of superabrasive volume 120 may comprise a catalyst-diminished region of a polycrystalline diamond volume. In addition, region 118 of superabrasive volume 120 may comprise a catalyst-containing region of a polycrystalline diamond volume. Accordingly, system 100, as shown in FIG. 4, may be utilized for exposing a polycrystalline diamond volume to a plurality of beta particles (i.e., beta particle exposure process 22, as shown in FIG. 6) and detecting a quantity of scattered beta particles (i.e., beta particle detection process 30, as shown in FIG. 6). Further, a boundary may be perceived between the catalyst-containing region of the polycrystalline diamond volume and a catalyst-diminished region of the polycrystalline diamond volume in response to detecting the quantity of scattered beta particles (i.e., boundary perception process 52, as shown in FIG. 6).

Figure 7:
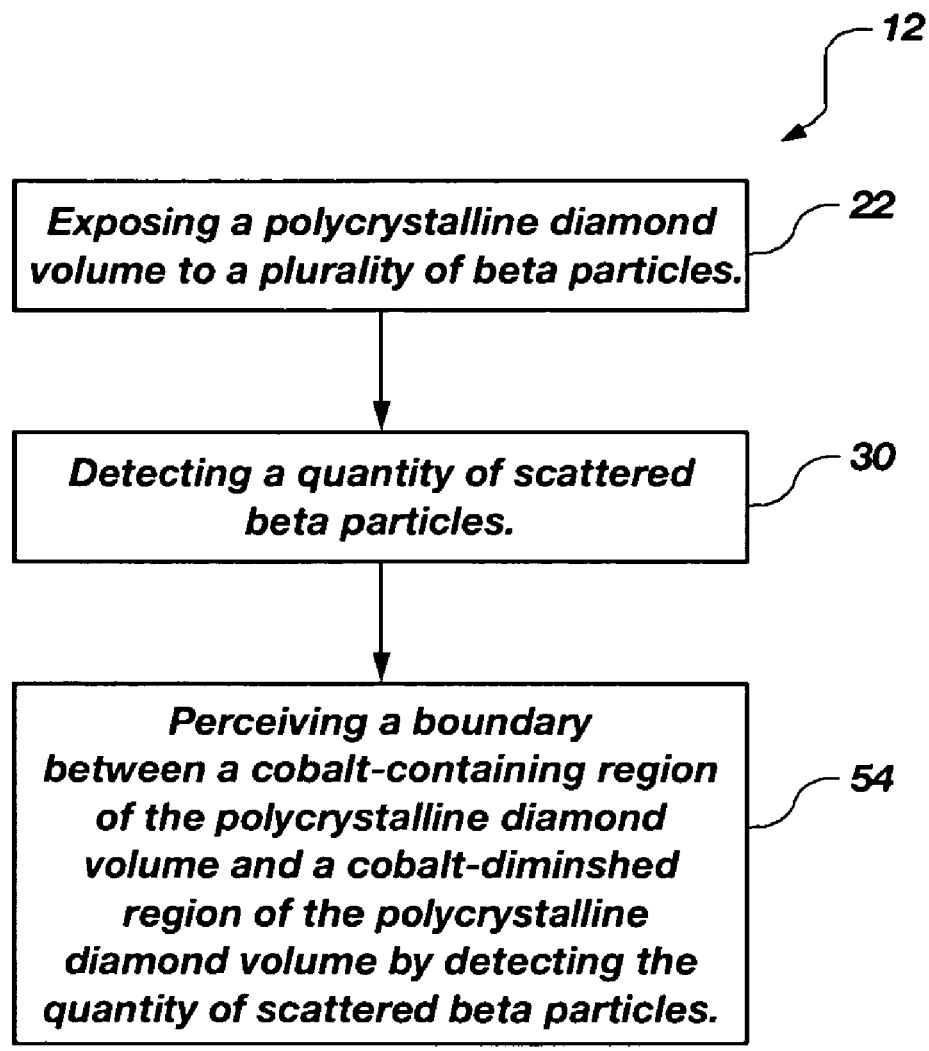
FIG. 7 shows a schematic flow chart of one embodiment of a method of evaluating a polycrystalline diamond volume comprising a cobalt-containing region and a cobalt-diminished region.

In one specific embodiment, a polycrystalline diamond volume may be formed with a catalyst comprising cobalt. Accordingly, as shown in FIG. 7, the present invention contemplates a method 12 for evaluating a polycrystalline diamond volume including a cobalt-containing region and a cobalt-diminished region. Particularly, as shown in FIG. 7, the present invention contemplates that a polycrystalline diamond volume may be exposed to a plurality of beta particles in a beta particle exposure process 22 and a quantity of scattered beta particles may be detected in beta particle detection process 30. Furthermore, in a boundary detection process 52, a boundary between a cobalt-containing region of the polycrystalline diamond volume and a cobalt-diminished region of the polycrystalline diamond volume may be perceived by detecting the quantity of scattered beta particles. As explained above, perceiving such a boundary may comprise measuring a depth to which a catalyst (e.g., cobalt, nickel, iron, etc.) has been at least partially removed from a region of the polycrystalline diamond volume.

Figure 8:
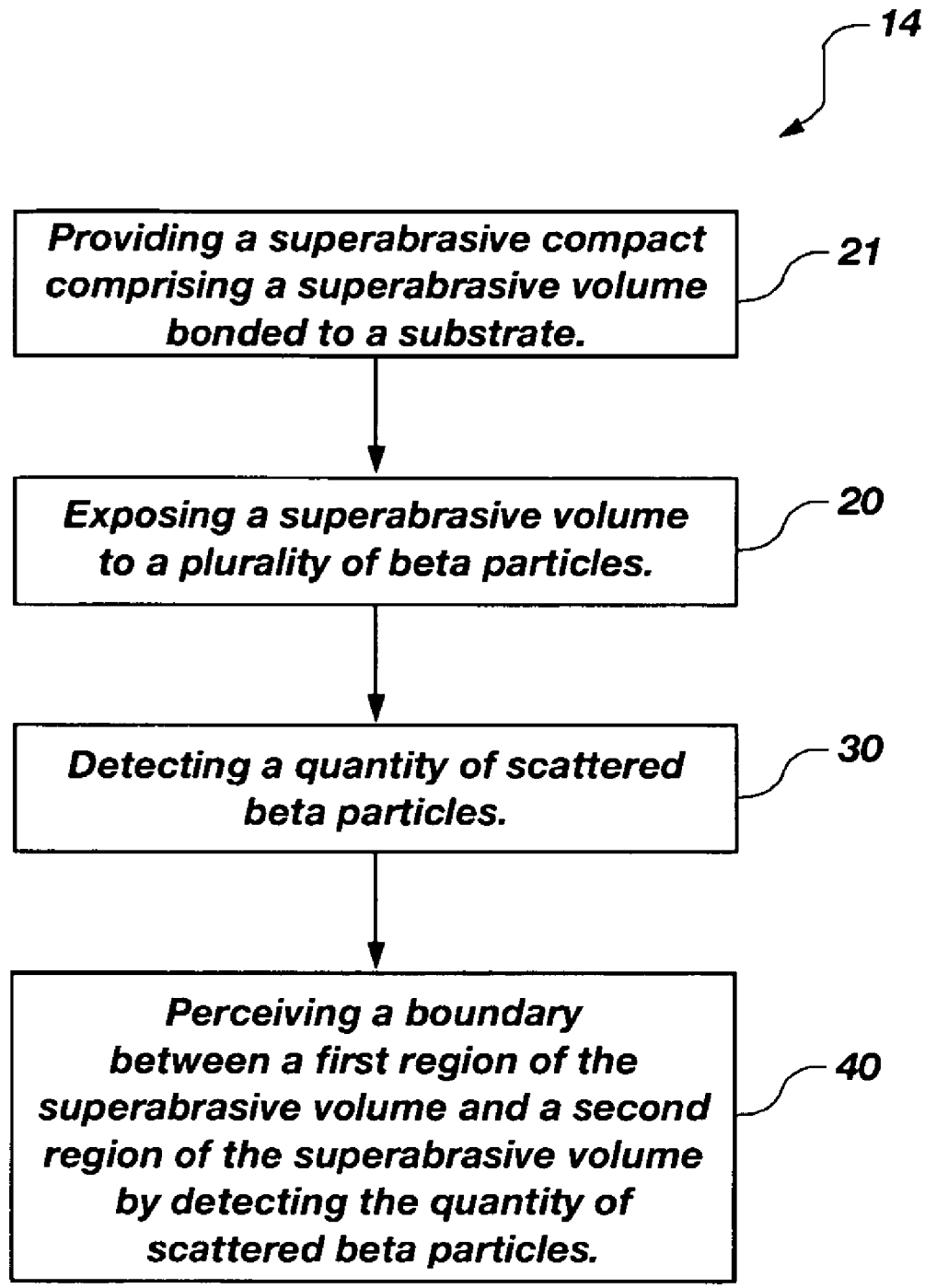
FIG. 8 shows a schematic flow chart of one embodiment of a method of evaluating a superabrasive compact comprising a superabrasive volume comprising a first region and a second region.

Another aspect of the present invention relates to evaluating a superabrasive compact comprising a superabrasive volume bonded to a substrate. Particularly, FIG. 8 shows a schematic flow chart depicting a method 14 of evaluating a superabrasive compact. More particularly, as shown in FIG. 8, a superabrasive compact comprising a superabrasive volume bonded to a substrate may be provided in providing action 21. In addition, the superabrasive volume may be exposed to a plurality of beta particles in a beta particle exposure process 20 and a quantity of scattered beta particles may be detected in a beta particle detection process 30. Also, a boundary perception process 40 may comprise perceiving a boundary between a first region of the superabrasive volume and a second region of the superabrasive volume by detecting the quantity of scattered beta particles.

Figure 9:
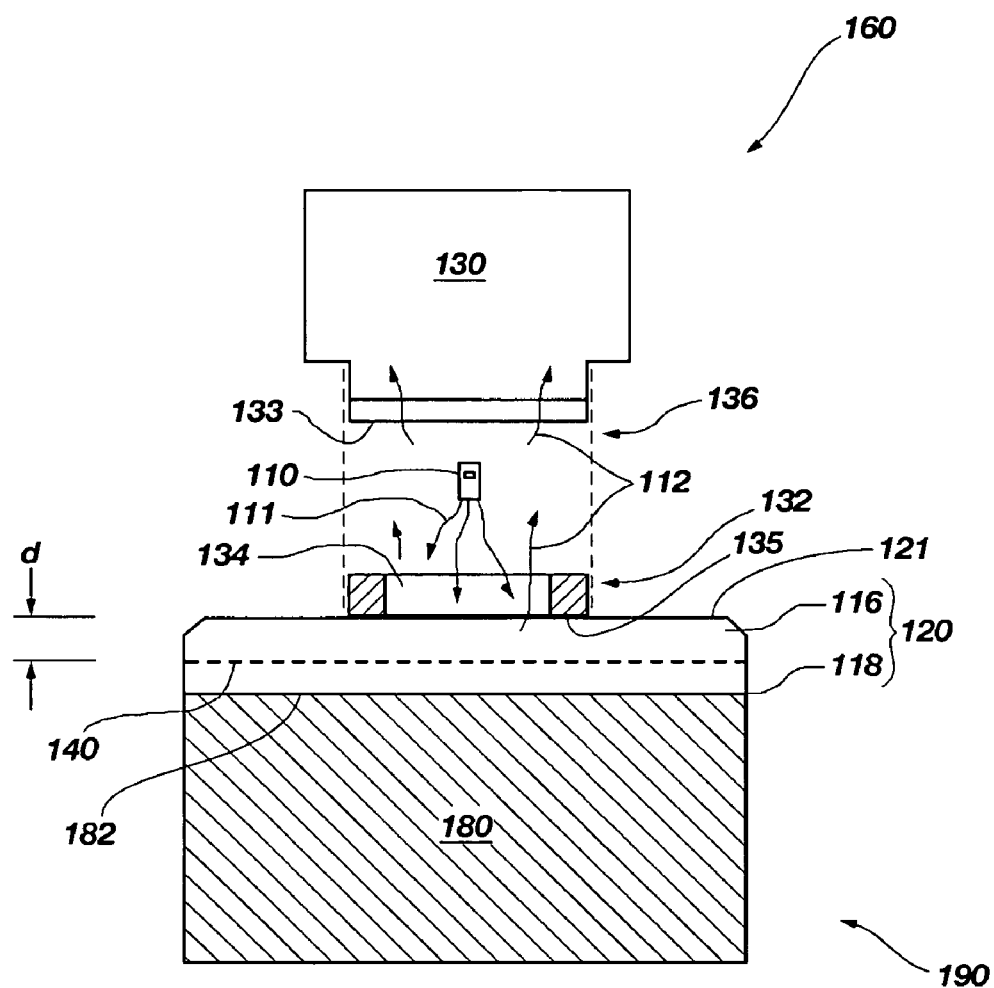
FIG. 9 shows a schematic, cross-sectional view of a beta particle evaluation system during use in evaluating a superabrasive compact.

FIG. 9 shows a schematic, side cross-sectional view of a probe 160 positioned proximate to a superabrasive compact 190 comprising a superabrasive volume 120 bonded to a substrate 180 along boundary 182. Accordingly, probe 160 in combination with other components (e.g., components comprising system 100, as shown in FIG. 4) may be utilized for perceiving a boundary 140 between a first region 116 of a superabrasive volume 120 of a superabrasive compact 190 and a second region 118 of the superabrasive volume 120 of a superabrasive compact 190, as shown in FIG. 9.

Figure 10:
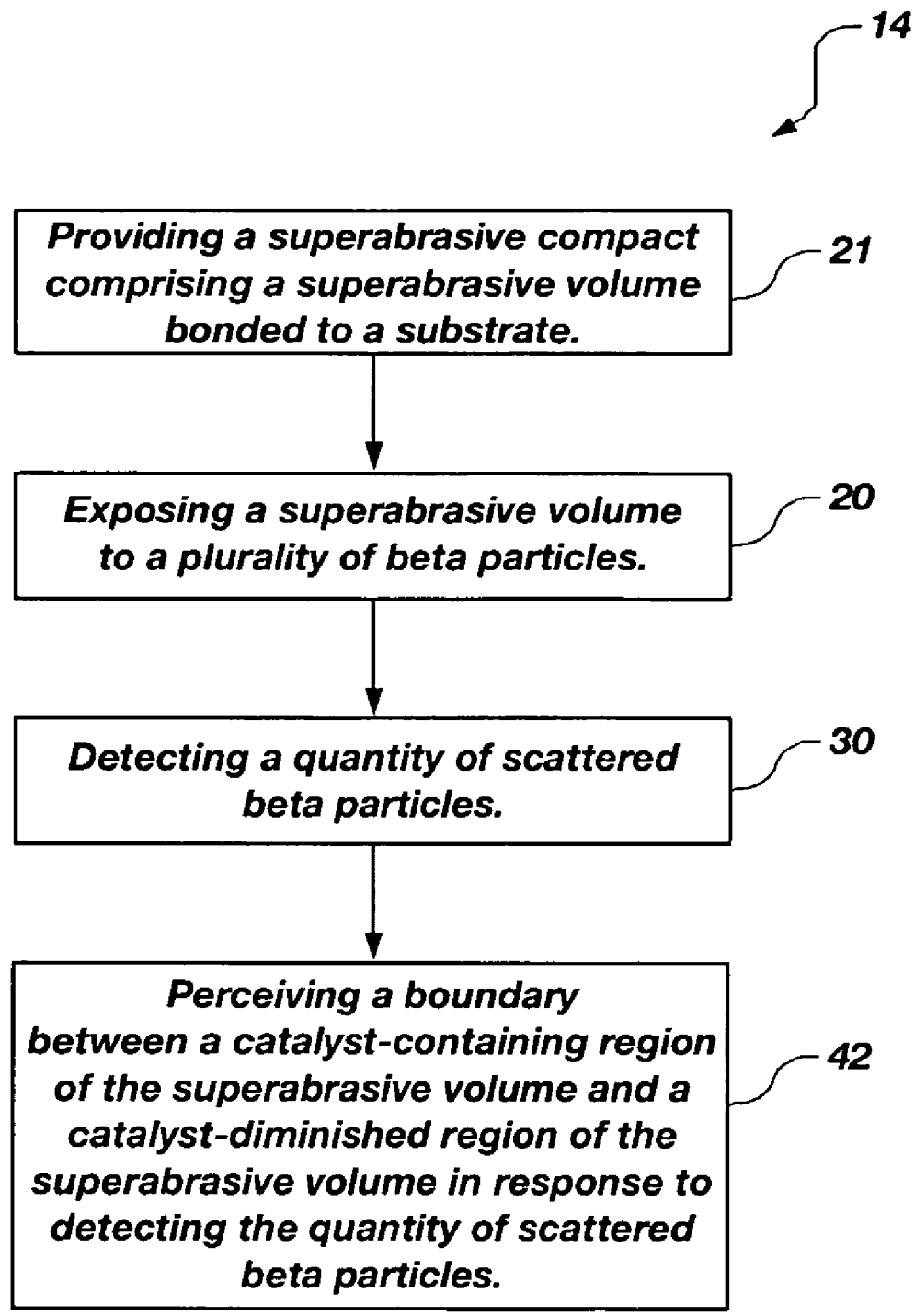
FIG. 10 shows a schematic flow chart of one embodiment of a method of evaluating a superabrasive compact comprising a superabrasive volume comprising a catalyst-containing region and a catalyst-diminished region.

In another embodiment, a boundary between a catalyst-containing region of the superabrasive volume and a catalyst-diminished region of the superabrasive volume may be perceived in response to detecting the quantity of scattered beta particles. More particularly, as shown in FIG. 10, a superabrasive compact comprising a superabrasive volume bonded to a substrate may be provided in providing action 21. In addition, the superabrasive volume may be exposed to a plurality of beta particles in a beta particle exposure process 20 and a quantity of scattered beta particles may be detected in a beta particle detection process 30. Also, a boundary perception process 42 may comprise perceiving a boundary between a catalyst containing region of the superabrasive volume and a catalyst-diminished region of the superabrasive volume by detecting the quantity of scattered beta particles.

Figure 11:
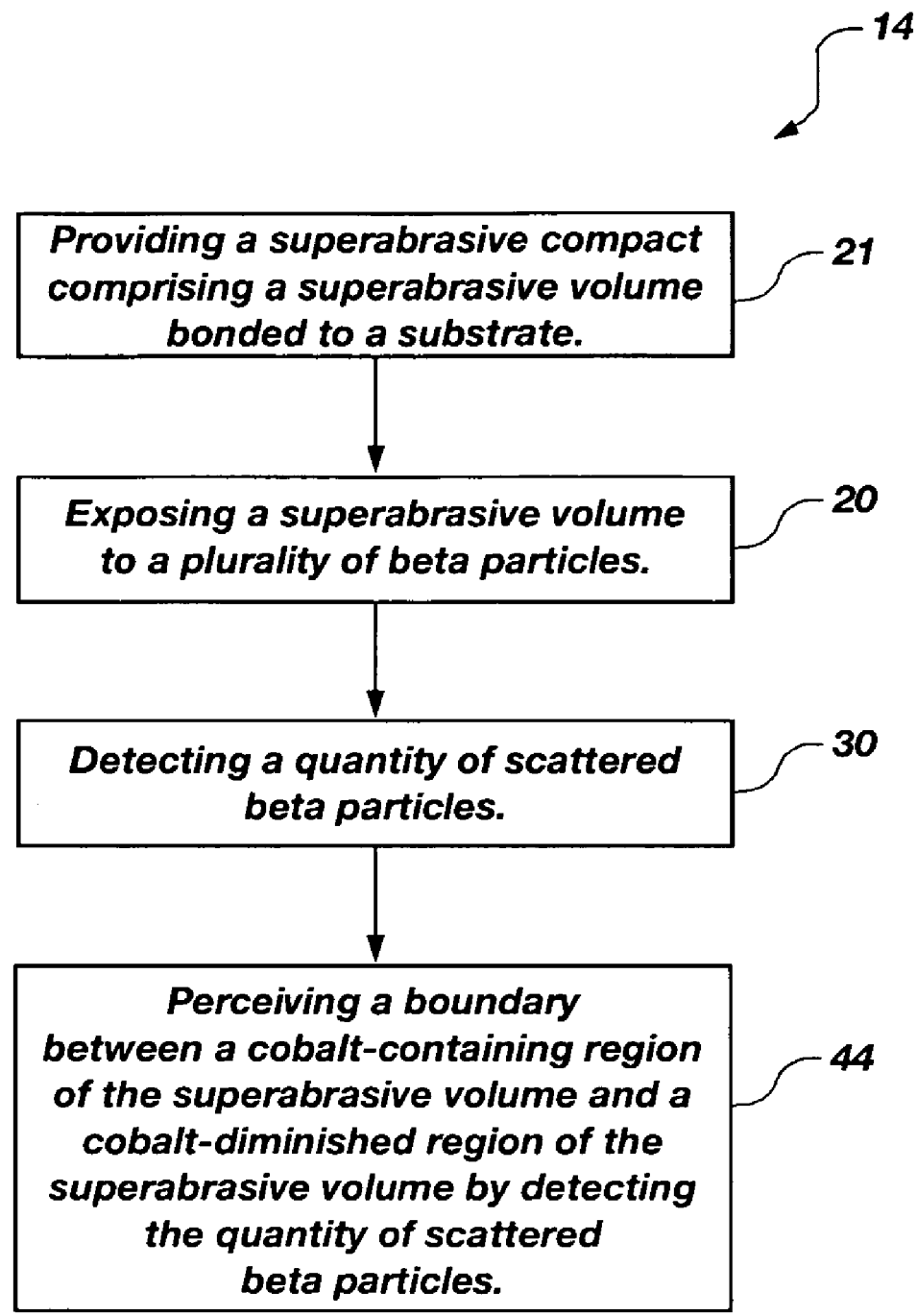
FIG. 11 shows a schematic flow chart of one embodiment of a method of evaluating a superabrasive compact comprising a superabrasive volume comprising a cobalt-containing region and a cobalt-diminished region.

In an additional embodiment, as shown in FIG. 11, a boundary between a cobalt-containing region of a superabrasive volume and a cobalt-diminished region of a superabrasive volume may be perceived by detecting a quantity of scattered beta particles. As shown in FIG. 11, a superabrasive compact comprising a superabrasive volume bonded to a substrate may be provided in providing action 21. In addition, the superabrasive volume may be exposed to a plurality of beta particles in a beta particle exposure process 20 and a quantity of scattered beta particles may be detected in a beta particle detection process 30. Also, a boundary perception process 40 may comprise perceiving a boundary between a cobalt-containing region of the superabrasive volume and a cobalt-diminished region of the superabrasive volume by detecting the quantity of scattered beta particles.

Figure 12:
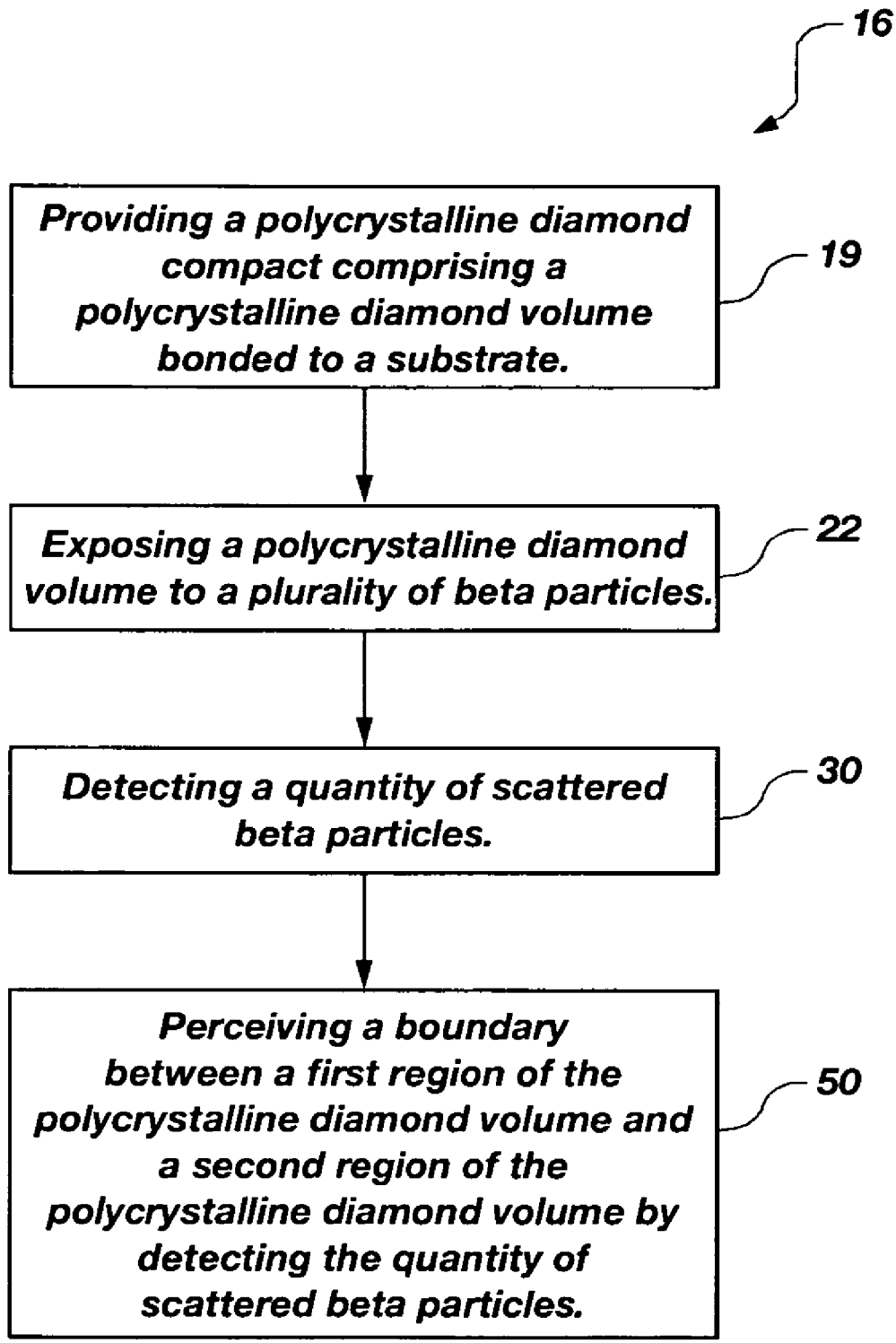
FIG. 12 shows a schematic flow chart of one embodiment of a method of evaluating a polycrystalline diamond compact comprising a polycrystalline diamond volume comprising a first region and a second region.

In yet another aspect of the present invention, a polycrystalline diamond compact comprising a polycrystalline diamond volume bonded to a substrate may be evaluated by utilizing beta particles. For example, FIG. 12 shows a schematic flow chart depicting a method 16 of evaluation of a polycrystalline diamond compact. Particularly, a polycrystalline diamond compact comprising a polycrystalline diamond volume bonded to a substrate may be provided, as depicted in providing action 19. Also, the polycrystalline diamond volume may be exposed to a plurality of beta particles, as depicted in beta particle exposure process 22, and a quantity of scattered beta particles may be detected, as depicted in beta particle detection process 30. A perception process 50 may comprise perceiving a boundary between a first region of the polycrystalline diamond volume and a second region of the polycrystalline diamond volume by detecting the quantity of scattered beta particles.

Figure 13:
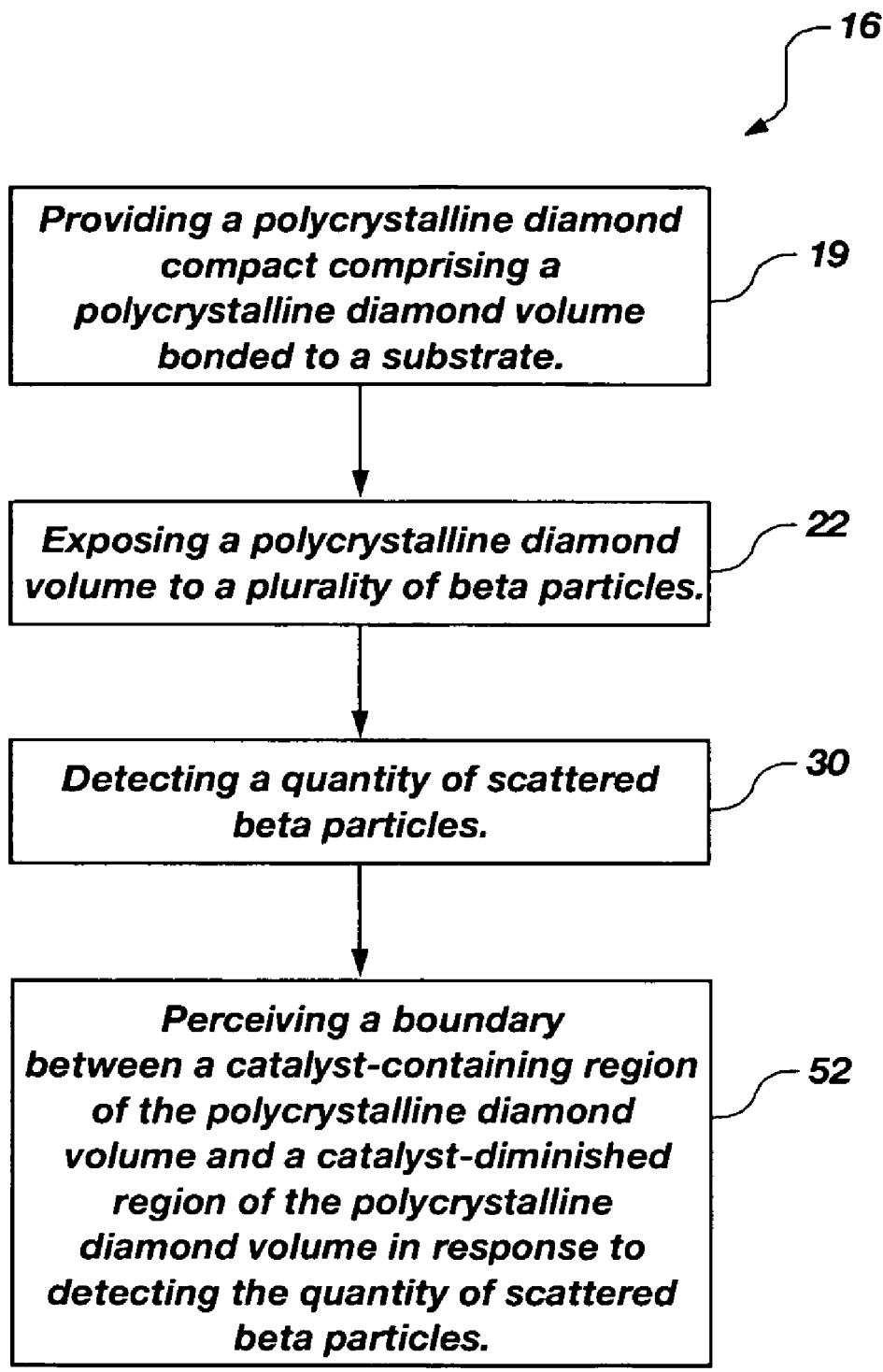
FIG. 13 shows a schematic flow chart of one embodiment of a method of evaluating a polycrystalline diamond compact comprising a polycrystalline diamond volume comprising a catalyst-containing region and a catalyst-diminished region.

Optionally, as shown in FIG. 13, a boundary between a catalyst-containing region of the superabrasive volume and a catalyst-diminished region of the superabrasive volume may be perceived in response to detecting the quantity of scattered beta particles. Specifically, FIG. 13 shows a schematic flow chart depicting a method 16 of evaluation of a polycrystalline diamond compact comprising providing a polycrystalline diamond volume bonded to a substrate, as depicted in providing action 19.

As described above, providing a polycrystalline diamond volume may comprise providing a polycrystalline diamond volume including a boundary between a region of a polycrystalline diamond layer including catalyst and a region of the polycrystalline diamond layer from which at least a portion of the catalyst has been removed. For instance, a catalyst (e.g., cobalt, nickel, iron, or any group VIII element, as denoted on the periodic chart, or any catalyst otherwise known in the art) used for forming the polycrystalline diamond layer may be at least partially removed from the polycrystalline diamond volume. Such a boundary (and associated region from which a catalyst is at least partially removed) may be formed by immersing (e.g., dipping or otherwise initiating contact between) a selected region of the polycrystalline diamond layer 20 and a liquid that is formulated to remove at least a portion of the catalyst. In one embodiment, the catalyst (e.g., cobalt, nickel, iron, etc.) may be substantially completely removed to form a region (e.g., a catalyst-diminished region). For example, as mentioned above, an acid may be used to leach at least a portion of the catalyst from a selected region of polycrystalline diamond volume. As one of ordinary skill in the art will appreciate, any metals (e.g., tungsten) in addition to the catalyst may be at least partially removed or substantially completely removed as well. The present invention further contemplates that electrolytic or electroless chemical processes, or any other processes known in the art, without limitation, may be employed for removing at least a portion of a catalyst from a selected region of a polycrystalline diamond layer 20.

As further shown in FIG. 13, the polycrystalline diamond volume may be exposed to a plurality of beta particles, as depicted in beta particle exposure process 22, and a quantity of scattered beta particles may be detected, as depicted in beta particle detection process 30. A perception process 50 may comprise perceiving a boundary between a catalyst-containing region of the polycrystalline diamond volume and a catalyst-diminished region of the polycrystalline diamond volume by detecting the quantity of scattered beta particles.

Figure 14:
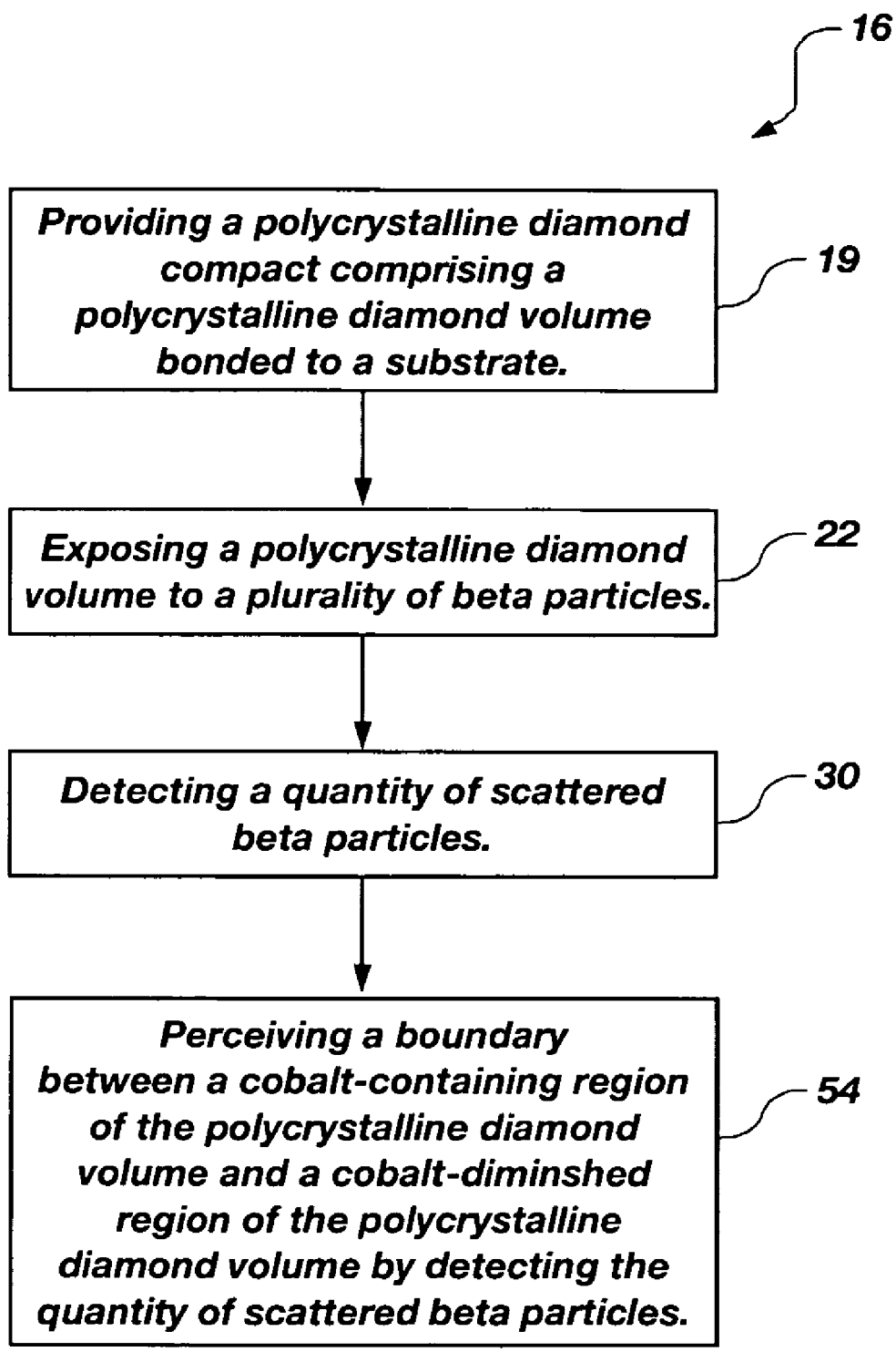
FIG. 14 shows a schematic flow chart of one embodiment of a method of evaluating a polycrystalline diamond compact comprising a polycrystalline diamond volume comprising a cobalt-containing region and a cobalt-diminished region.

As a further optional embodiment, as shown in FIG. 14, a boundary between a cobalt-containing region of the superabrasive volume and a cobalt-diminished region of the superabrasive volume may be perceived in response to detecting the quantity of scattered beta particles. FIG. 14 shows a schematic flow chart depicting a method 16 of evaluation comprising providing a polycrystalline diamond volume bonded to a substrate, as depicted in providing action 19. As described above, providing a polycrystalline diamond volume may comprise providing a polycrystalline diamond volume including a boundary between a region of a polycrystalline diamond layer including catalyst and a region of the polycrystalline diamond layer from which at least a portion of the catalyst has been removed. In addition, the polycrystalline diamond volume may be exposed to a plurality of beta particles, as depicted in beta particle exposure process 22, and a quantity of scattered beta particles may be detected, as depicted in beta particle detection process 30. A perception process 50 may comprise perceiving a boundary between a cobalt-containing region of the polycrystalline diamond volume and a cobalt-diminished region of the polycrystalline diamond volume by detecting the quantity of scattered beta particles.

Figure 15:
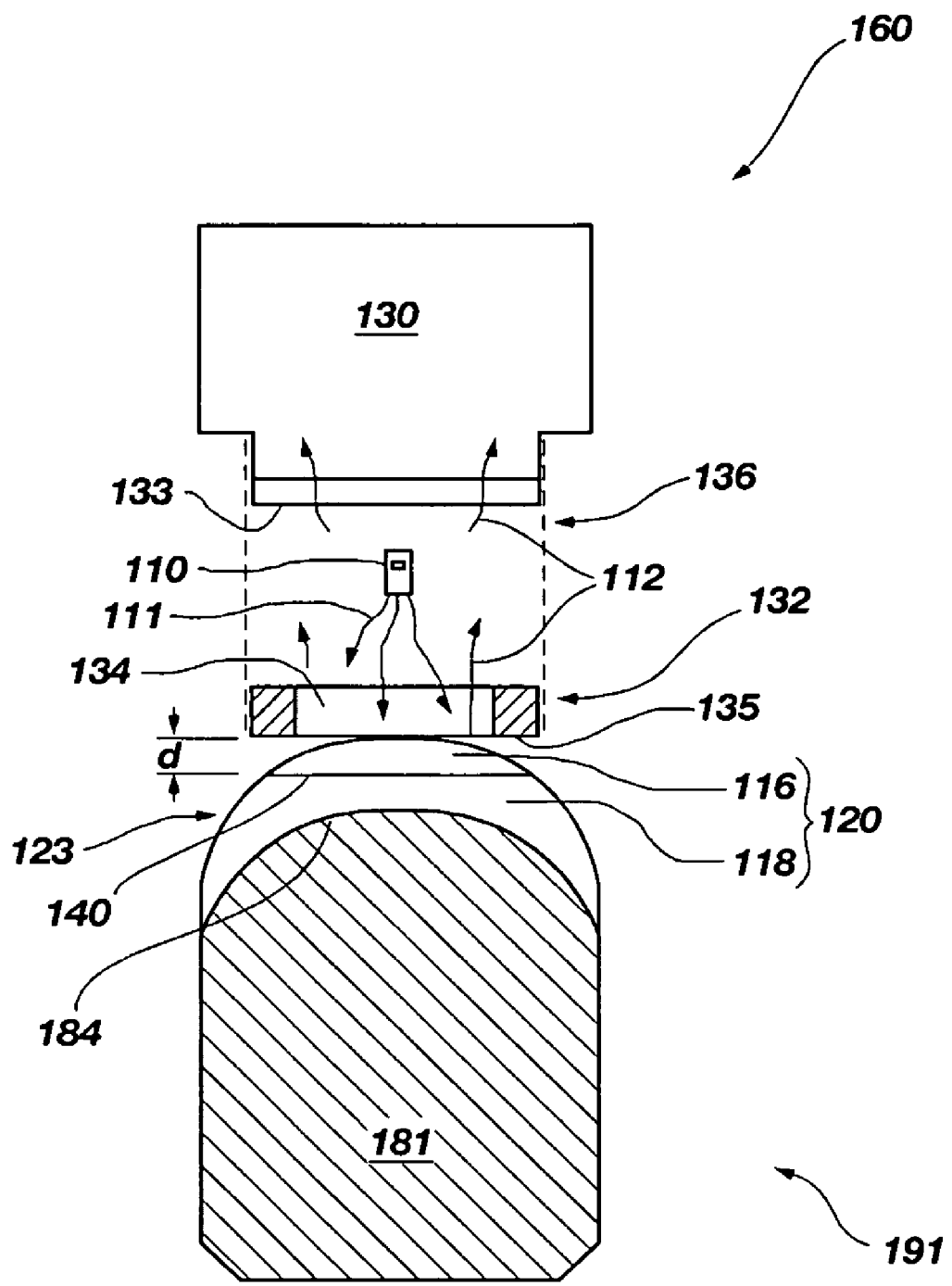
FIG. 15 shows a schematic, cross-sectional view of a beta particle evaluation system during use in evaluating one embodiment of a superabrasive compact comprising an arcuate exterior surface.

As mentioned above, a variety of material-related characteristics as well as geometry-related aspects may influence the use of beta particles for perceiving a boundary within a superabrasive volume. The present invention contemplates that any superabrasive volume, superabrasive compact, or any other superabrasive article may be evaluated by employing beta particles. For example, the present invention contemplates that a superabrasive compact comprising a superabrasive volume including an arcuate exterior surface may be evaluated by employing beta particles. Specifically, FIG. 15 shows a schematic, side cross-sectional view of probe 160 positioned adjacent to superabrasive compact 191, the superabrasive compact 191 comprising a superabrasive volume 120 bonded to a substrate 181. Thus, as shown in FIG. 15, a depth d may be measured between an arcuate exterior surface 123 and boundary 140. Any of the above-discussed embodiments may be employed for perceiving boundary 140.

In addition, any superabrasive compact disclosed in U.S. application Ser. No. 11/333,969, filed 17 Jan. 2006, the disclosure of which is incorporated, in its entirety, by this reference, may be evaluated by any method or system disclosed herein.

Figure 16:
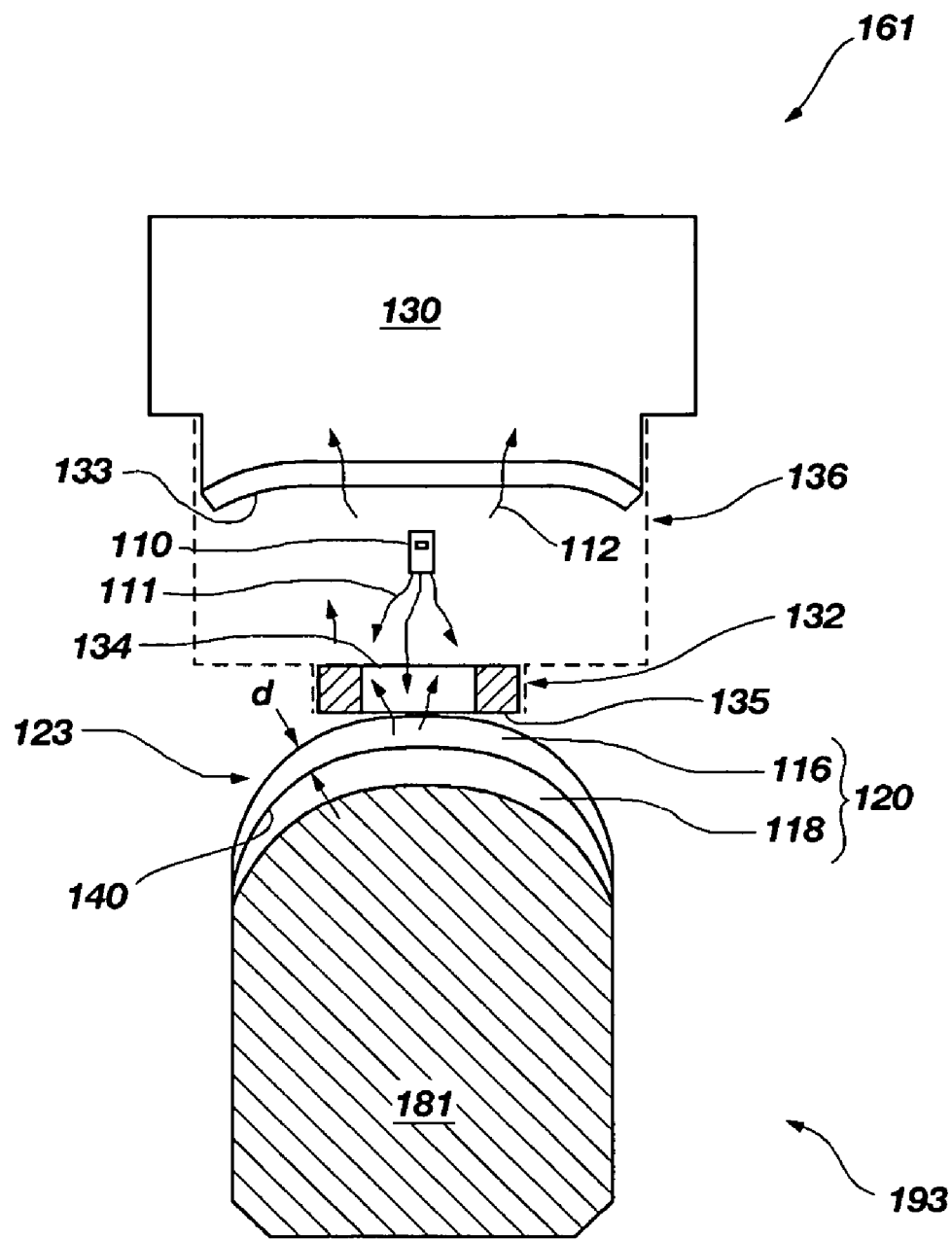
FIG. 16 shows a schematic, cross-sectional view of a beta particle evaluation system during use in evaluating another embodiment of a superabrasive compact comprising an arcuate exterior surface.

As shown in FIG. 15, boundary 140 may be substantially planar in one embodiment. However, the present invention is not so limited. Rather, the present invention contemplates that beta particles may be employed for perceiving (e.g., measuring, quantifying, or characterizing) a non-planar boundary. For example, FIG. 16 shows a schematic, side cross-sectional view of a probe 161 positioned proximate to a superabrasive compact 193 comprising a superabrasive volume 120 bonded to a substrate 181. Accordingly, as shown in FIG. 16, a depth d may be measured between an arcuate exterior surface 123 and boundary 140. Any of the above-discussed embodiments may be employed for perceiving boundary 140.

As one of ordinary skill in the art will appreciate, correlation of a quantity of scattered beta particles to a given depth d of boundary 140 from arcuate exterior surface 123 may be different in comparison to calibration data or algorithms developed for substantially planar boundaries. In addition, FIG. 16 shows a metering port 132 that is smaller than the metering ports shown in FIGS. 4, 9, and 15. Also, as shown in FIG. 16, detector 130 may be sized and configured advantageously for a given application. For example, as shown in FIG. 16, detector 130 may be larger than the detectors shown in FIGS. 4, 9, and 15 and may also include a detector surface 133 that is at least partially arcuate (e.g., concave, convex, etc.). One of ordinary skill in the art will appreciate that calibration data and/or algorithms for perceiving a substantially planar boundary may differ from calibration data and/or algorithms for perceiving an arcuate boundary (e.g., at least a portion of an arcuate boundary surface).

Thus, the present invention contemplates that a beta particle source, a metering port, and a beta particle detector may be tailored for a given application. Additionally, one of ordinary skill in the art will appreciate that more than one boundary formed between adjacent regions of a superabrasive volume may be perceived or measured by the above-described methods. For example, different beta particle sources (i.e., beta particle sources emitting particles with different energy levels) may be employed for perceiving a plurality of boundaries located at different, respective positions within a superabrasive volume. Many variations are contemplated by the present invention.

Figure 17:
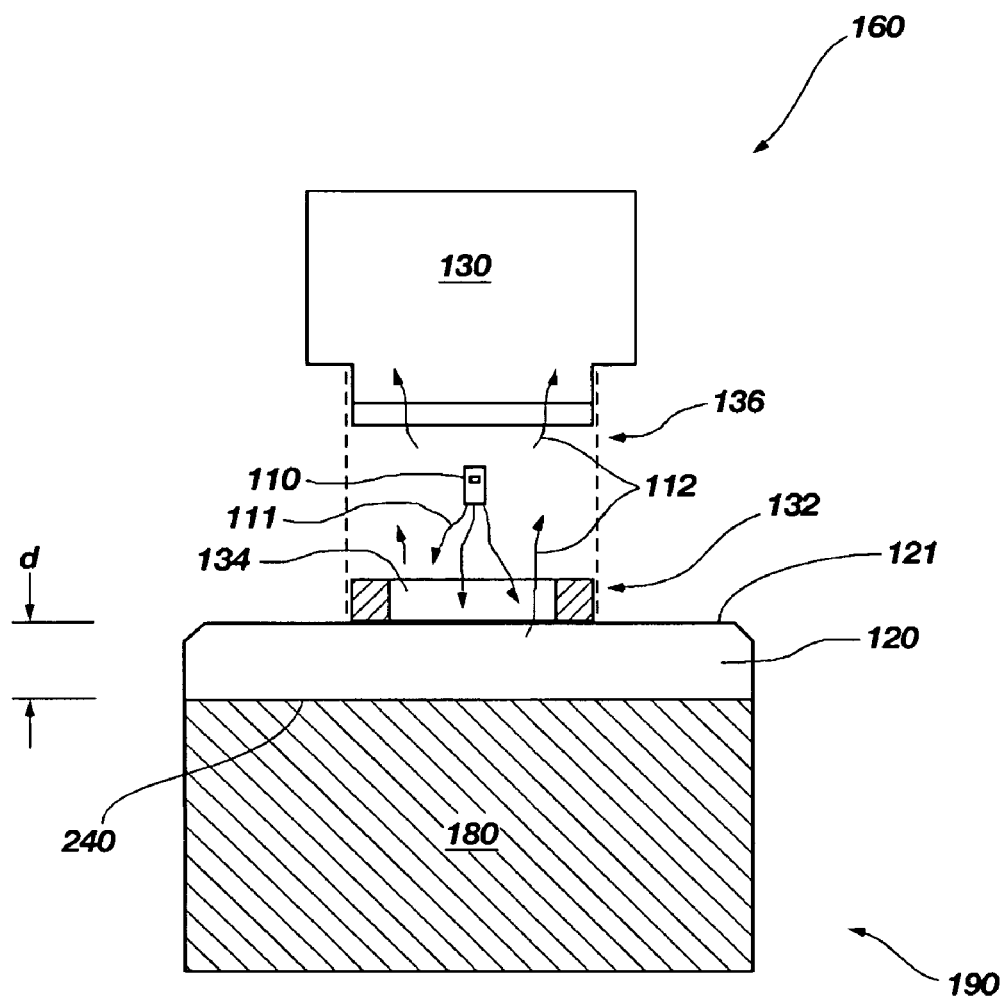
FIG. 17 shows a schematic, cross-sectional view of a beta particle evaluation system during use in evaluating a boundary between a superabrasive volume and a substrate.

Another aspect of the present invention relates to perceiving a boundary between a superabrasive volume and a substrate. For example, FIG. 17 shows a schematic, side cross-sectional view of a probe 160 positioned proximate to a superabrasive compact comprising a superabrasive volume 120 bonded to a substrate 180 along boundary 240. In one embodiment, superabrasive volume 120 may comprise a polycrystalline diamond volume from which a catalyst (e.g., cobalt, nickel, iron, etc.) may be at least partially removed or substantially completely removed. Optionally, substrate 180 may comprise a cemented tungsten carbide material (e.g., a cobalt cemented tungsten carbide, any other known cemented tungsten carbide, or any other substrate as known in the art). Thus, beta particles may be emitted from beta source 110 and may be scattered through interaction with boundary 240. Further, detector 130 may detect scattered beta particles and measurement of a quantity of such scattered beta particles may be correlated to a depth d between upper surface 121 of superabrasive volume 120 and boundary 240. Any of the above-discussed embodiments may be employed for perceiving boundary 240. As known in the art, boundary 240 may be non-planar, planar, or a combination of non-planar and planar features.

Figure 18:
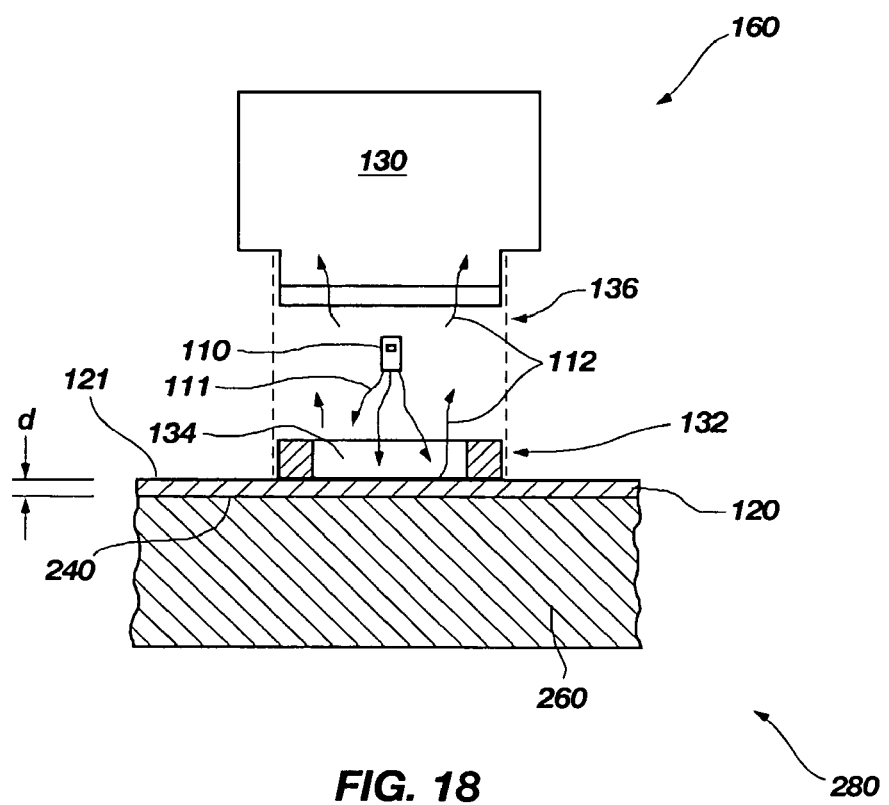
FIG. 18 shows a schematic, cross-sectional view of a beta particle evaluation system during use in evaluating a superabrasive layer formed on a base element.

In yet a further aspect of the present invention, beta particles may be utilized for perceiving a boundary formed between a superabrasive layer and a base element. For example, FIG. 18 shows a schematic, side cross-sectional view of a probe 160 positioned adjacent to an article 280 comprising a base element 260 and a superabrasive layer 220 formed upon the base element 260. Thus, as explained above, beta particles may interact with boundary 240 and may be scattered and detected by detector 130 to perceive boundary 240, as described above. Any of the above-discussed embodiments may be employed for perceiving boundary 240.

One of ordinary skill in the art will understand that any of the above-discussed methods and systems may provide the ability to nondestructively evaluate a superabrasive volume. Thus, characteristics of a superabrasive volume that is evaluated via scattered beta particles may be substantially unaffected by interaction with beta particles. Thus, such methods and systems may provide advantage over conventional methods and systems configured for destructive evaluation of superabrasive volumes. Further, although the methods and systems described above have been discussed in the context of superabrasive structures (e.g., comprising polycrystalline diamond), the present invention is not so limited, and one of ordinary skill in the art will appreciate that the discussed methods and structures could be used for varied applications as known in the art, without limitation. In addition, while certain embodiments and details have been included herein for purposes of illustrating aspects of the instant disclosure, it will be apparent to those skilled in the art that various changes in the systems, apparatuses, and methods disclosed herein may be made without departing from the scope of the instant disclosure, which is defined, at least in part, in the appended claims. The words "including" and "having," as used herein including the claims, shall have the same meaning as the word "comprising."

What is claimed is:

1. A method of evaluating a superabrasive volume, the method comprising:
   providing a superabrasive volume comprising a plurality of superabrasive grains bonded to one another forming a coherent matrix;
   exposing a superabrasive volume to beta particles;
   detecting a quantity of scattered beta particles;
   perceiving a boundary between a first region of the superabrasive volume and a second region of the superabrasive volume in response to detecting the quantity of scattered beta particles wherein each of the first volume and the second volume include a portion of the coherent matrix, and wherein perceiving the boundary between the first region and the second region of the superabrasive volume comprises perceiving a boundary between a catalyst-containing region and a catalyst-diminished region of the superabrasive volume.

2. The method of claim 1, wherein perceiving the boundary comprises perceiving an arcuate boundary.

3. The method of claim 1, wherein exposing the superabrasive volume to beta particles comprises exposing a polycrystalline diamond volume to beta particles.

4. The method of claim 3, wherein a catalyst used for forming the polycrystalline diamond volume is substantially removed from the first region of the polycrystalline diamond volume.

5. The method of claim 4, wherein perceiving the boundary between the first region of the superabrasive volume and the second region of the superabrasive volume comprises measuring a depth of the first superabrasive region from an exterior surface of the polycrystalline diamond volume.

6. The method of claim 4, wherein cobalt is substantially removed from the first region of the polycrystalline diamond volume.

7. The method of claim 1, wherein perceiving the boundary between the first region and the second region of the superabrasive volume comprises perceiving a boundary between a cobalt-containing region and a cobalt-diminished region of the superabrasive volume.

8. A method of evaluating a polycrystalline diamond volume, the method comprising:
 exposing a polycrystalline diamond volume to beta particles;
 detecting a quantity of scattered beta particles;
 perceiving a boundary between a catalyst-containing region of the polycrystalline diamond volume and a catalyst-diminished region of the polycrystalline diamond volume in response to detecting the quantity of scattered beta particles.

9. The method of claim 8, wherein perceiving the boundary comprises perceiving an arcuate boundary.

10. The method of claim 8, wherein perceiving the boundary comprises measuring a depth of the catalyst-diminished region from an exterior surface of the polycrystalline diamond volume.

11. The method of claim 8, wherein cobalt is substantially removed from the catalyst-diminished region of the polycrystalline diamond volume.

12. The method of claim 8, wherein perceiving the boundary between the catalyst-diminished region and the catalyst-containing region of the polycrystalline diamond volume comprises perceiving a boundary between a cobalt-containing region and a cobalt-diminished region of the polycrystalline diamond volume.

13. A method of evaluating a polycrystalline diamond compact, the method comprising:
 providing a polycrystalline diamond compact comprising a polycrystalline diamond volume bonded to a substrate;
 exposing the polycrystalline diamond volume to beta particles;
 detecting a quantity of scattered beta particles;
 perceiving a boundary between a catalyst-containing region of the polycrystalline diamond volume and a catalyst-diminished region of the polycrystalline diamond volume in response to detecting the quantity of scattered beta particles.

14. The method of claim 13, wherein perceiving the boundary comprises perceiving an arcuate boundary.

15. The method of claim 13, wherein perceiving the boundary between the catalyst-containing region of the polycrystalline diamond volume and the catalyst-diminished region of the polycrystalline diamond volume comprises measuring a depth of the catalyst-diminished region from an exterior surface of the polycrystalline diamond volume.

16. The method of claim 13, wherein a catalyst used for forming the polycrystalline diamond volume is substantially removed from the catalyst-diminished region of the polycrystalline diamond volume.

17. The method of claim 13, wherein cobalt is substantially removed from the catalyst-diminished region of the polycrystalline diamond volume.

18. The method of claim 13, wherein perceiving the boundary between the catalyst-containing region and the catalyst-diminished region of the polycrystalline diamond volume comprises perceiving a boundary between a cobalt-containing region and a cobalt-diminished second of the polycrystalline diamond volume.

19. A method of evaluating a polycrystalline diamond compact, the method comprising:
 providing a polycrystalline diamond compact comprising a polycrystalline diamond volume bonded to a substrate, the polycrystalline diamond volume including a coherent matrix of mutually bonded diamond grains and a catalyst material in a portion of the polycrystalline diamond volume;
 exposing the polycrystalline diamond volume to beta particles;
 detecting a quantity of scattered beta particles;
 measuring a depth to which a catalyst-diminished region of the polycrystalline diamond extends within the polycrystalline diamond volume in response to detecting the quantity of scattered beta particles.

20. The method of claim 19, wherein measuring the depth to which the catalyst-diminished region of the polycrystalline diamond extends within the polycrystalline diamond volume comprises measuring a depth to which cobalt has been at least partially removed from the polycrystalline diamond volume.

21. A system configured to evaluate a superabrasive volume, the system comprising:
 a beta particle source;
 a beta particle detector;
 calibration data for correlating a quantity of detected beta particles to an indicated depth of a first region of a coherent matrix of a superabrasive volume, the indicated depth being less than a total thickness of the coherent matrix.

22. The system of claim 21, wherein the calibration data comprises a first measured quantity of beta particles associated with a first depth and at least a second measured quantity of beta particles associated with a second depth.

23. The system of claim 21, wherein the calibration data is designed to correlate the quantity of detected beta particles to the indicated depth of a first region of a polycrystalline diamond volume.

24. The system of claim 23, wherein the calibration data is designed to correlate the quantity of detected beta particles to the indicated depth of a catalyst-diminished region of the polycrystalline diamond volume.

25. The system of claim 23, wherein the calibration data is designed to correlate the quantity of detected beta particles to the indicated depth of a cobalt-diminished region of the polycrystalline diamond volume.

* * * * *